United States Patent
Enomoto et al.

(10) Patent No.: US 10,349,913 B2
(45) Date of Patent: Jul. 16, 2019

(54) RADIOGRAPHY APPARATUS, RADIOGRAPHY METHOD, AND RADIOGRAPHY PROGRAM

(71) Applicant: FUJIFILM CORPORATION, Minato-ku, Tokyo (JP)

(72) Inventors: Jun Enomoto, Kanagawa (JP); Noriaki Ida, Kanagawa (JP); Daiki Harada, Kanagawa (JP); Takahiro Kawamura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 210 days.

(21) Appl. No.: 15/239,843

(22) Filed: Aug. 18, 2016

(65) Prior Publication Data

US 2016/0354050 A1    Dec. 8, 2016

Related U.S. Application Data

(63) Continuation of application No. PCT/JP2015/059776, filed on Mar. 27, 2015.

(30) Foreign Application Priority Data

Mar. 28, 2014  (JP) ................................ 2014-070544

(51) Int. Cl.
    *A61B 6/00*    (2006.01)
(52) U.S. Cl.
    CPC .......... *A61B 6/5282* (2013.01); *A61B 6/4283* (2013.01); *A61B 6/4291* (2013.01);
    (Continued)

(58) Field of Classification Search
    CPC ... A61B 6/4283; A61B 6/4291; A61B 6/4405; A61B 6/461; A61B 6/467; A61B 6/5282; A61B 6/563; A61B 6/54
    See application file for complete search history.

(56) References Cited

U.S. PATENT DOCUMENTS

| 2010/0046822 A1* | 2/2010 | Li ........................ A61B 6/5282 382/132 |
| 2015/0251018 A1* | 9/2015 | Tajima ................. A61B 6/5282 378/28 |

(Continued)

FOREIGN PATENT DOCUMENTS

| JP | H05-82111 B2 | 11/1993 |
| JP | H10-112399 A | 4/1998 |

(Continued)

*Primary Examiner* — Chih-Cheng Kao
(74) *Attorney, Agent, or Firm* — Solaris Intellectual Property Group, PLLC

(57) ABSTRACT

A derivation unit derives imaging conditions corresponding to virtual grid characteristics (grid ratio) received by a receiving unit on the basis of a table stored in a storage unit. The derivation unit sets the derived imaging conditions in a radiation source control unit. The radiation source control unit controls a radiation source on the basis of the set imaging conditions such that a radiographic image is captured. An execution unit of an image processing device acquires the radiographic image captured by the radiation detector through a detector control unit. The execution unit performs a virtual grid process for the acquired radiographic image on the basis of the virtual grid characteristics received by the receiving unit and the imaging conditions derived by the derivation unit to generate a radiographic image from which the influence of scattered radiation has been removed and displays the radiographic image on a display unit.

9 Claims, 6 Drawing Sheets

| | GRID CHARACTERISTICS | SUBJECT INFORMATION | | | IMAGING CONDITIONS | | |
|---|---|---|---|---|---|---|---|
| | GRID RATIO | AGE | BODY TYPE | PART TO BE IMAGED | TUBE VOLTAGE | TUBE CURRENT | IRRADIATION TIME |
| (EXAMPLE 1) | 3:1 | ADULT | NORMAL BODY TYPE | CHEST | $\alpha$ kVp | $\beta$ mA | $\gamma$ msec |
| (EXAMPLE 2) | 3:1 | ADULT | FAT BODY TYPE | CHEST | $\alpha + \theta$ kVp | $\beta$ mA | $\gamma$ msec |

(52) U.S. Cl.
CPC ............ *A61B 6/4405* (2013.01); *A61B 6/461* (2013.01); *A61B 6/467* (2013.01); *A61B 6/54* (2013.01); *A61B 6/563* (2013.01)

(56) References Cited

U.S. PATENT DOCUMENTS

| | | | | |
|---|---|---|---|---|
| 2015/0379711 A1* | 12/2015 | Imai | ...................... | A61B 6/5282 |
| | | | | 382/132 |
| 2016/0081648 A1* | 3/2016 | Tajima | ................. | A61B 6/5282 |
| | | | | 378/165 |
| 2016/0354051 A1* | 12/2016 | Enomoto | ............. | A61B 6/4241 |

FOREIGN PATENT DOCUMENTS

| | | | |
|---|---|---|---|
| JP | H10-262961 | A | 10/1998 |
| JP | 2002-186614 | A | 7/2002 |
| JP | 2004-329783 | A | 11/2004 |
| JP | 2010-501238 | A | 1/2010 |
| JP | 2013-172881 | A | 9/2013 |

\* cited by examiner

FIG. 2

| GRID CHARACTERISTICS | SUBJECT INFORMATION | | | IMAGING CONDITIONS | | |
|---|---|---|---|---|---|---|
| GRID RATIO | AGE | BODY TYPE | PART TO BE IMAGED | TUBE VOLTAGE | TUBE CURRENT | IRRADIATION TIME |
| (EXAMPLE 1) 3:1 | ADULT | NORMAL BODY TYPE | CHEST | $\alpha$ kVp | $\beta$ mA | $\gamma$ msec |
| (EXAMPLE 2) 3:1 | ADULT | FAT BODY TYPE | CHEST | $\alpha + \theta$ kVp | $\beta$ mA | $\gamma$ msec |

RADIOGRAPHY APPARATUS, RADIOGRAPHY METHOD, AND RADIOGRAPHY PROGRAM

CROSS-REFERENCE TO RELATED APPLICATIONS

This application is a continuation application of International Application No. PCT/JP2015/059776, filed on Mar. 27, 2015, which is incorporated herein by reference in its entirety. Further, this application claims priority from Japanese Patent Application No. 2014-070544, filed on Mar. 28, 2014, the disclosure of which is incorporated by reference herein in its entirety.

BACKGROUND

Technical Field

The present invention relates to a radiography apparatus, a radiography method, and a radiography program.

Related Art

In the related art, in a case in which a radiographic image of a subject is captured using radiation that is transmitted through the subject, particularly, in a case in which the thickness of the subject is large, the radiation is scattered in the subject and the scattered radiation (hereinafter, also referred to a "scattered ray") causes a reduction in the contrast of the captured radiographic image. For this reason, in some cases, a scattered radiation removal grid (hereinafter, simply referred to as a grid) is provided between a subject and a radiation detector in order to reduce the influence of scattered radiation in the capture of a radiographic image. When imaging is performed using the grid, radiation which is scattered by the subject is less likely to reach the radiation detector. Therefore, it is possible to improve the contrast of the radiographic image (for example, see Japanese Patent Application Publication (JP-B) No. H05-82111, Japanese Patent Application Laid-Open (JP-A) No. 10-262961, and JP-A No. 2004-329783).

In a case in which a radiographic image is captured using the grid, imaging conditions are determined according to the characteristics of the grid used. Therefore, in some cases, when an operation of setting the imaging conditions corresponding to the characteristics of the grid used is performed, the burden of the operation on a user, such as a technician or a doctor, increases.

However, when imaging is performed using the grid as in the related art, a subject image and a fine stripe pattern (moire) corresponding to the grid are included in a radiographic image, which makes it difficult to see a captured radiographic image. Image processing for removing the stripe pattern is also known (for example, see JP-A No. 2013-172881). In some cases, the processing time increases.

There is a technique that performs image processing for a radiographic image which has been captured, without providing a grid between the subject and a radiation detector, to remove the influence of scattered radiation. In addition, the characteristics of the grid that is assumed to be used can be designated and the amount of removal of scattered radiation can be controlled. Hereinafter, a process that performs image processing on the basis of the characteristics of a grid, which is assumed to be used, to remove the influence of scattered radiation to the same extent as that in a case in which a grid is provided is referred to as a virtual grid process.

In a case in which imaging is performed using the virtual grid process, the imaging conditions are determined according to the characteristics of the grid that is assumed to be used, as in a case in which imaging is performed using a grid. As a result, the burden of an operation on the user increases.

SUMMARY

The invention provides a radiography apparatus, a radiography method, and a radiography program that can reduce the burden of an operation related to the setting of imaging conditions on a user.

According to a first aspect of the invention, there is provided a radiography apparatus that performs a scattered radiation removal process of removing an influence of scattered radiation included in radiation which has passed through a subject for a radiographic image captured by irradiating the subject with the radiation. The radiography apparatus include: a receiving unit that receives virtual grid characteristics which are characteristics of a grid virtually used to remove the scattered radiation in the capture of the radiographic image and are used to set an amount of removal of the scattered radiation; and a derivation unit that derives imaging conditions of the radiographic image according to the virtual grid characteristics received by the receiving unit.

According to a second aspect of the invention, the radiography apparatus according to the first aspect may further include an imaging unit that captures the radiographic image under the imaging conditions derived by the derivation unit.

According to a third aspect of the invention, the radiography apparatus according to the second aspect may further include an execution unit that performs the scattered radiation removal process for the radiographic image captured by the imaging unit with an amount of removal corresponding to the virtual grid characteristics.

According to a fourth aspect of the invention, in the third aspect, during a re-imaging process, the execution unit may perform the scattered radiation removal process on the basis of the virtual grid characteristics received in a previous imaging process.

According to a fifth aspect of the invention, the radiography apparatus according to any one of the first to fourth aspects may further include a storage unit that stores the virtual grid characteristics and the imaging conditions corresponding to the virtual grid characteristics so as to be associated with each other. The derivation unit may read the imaging conditions corresponding to the virtual grid characteristics received by the receiving unit from the storage unit and derive the imaging conditions.

According to a sixth aspect of the invention, in any one of the first to fifth aspects, the derivation unit may derive the imaging conditions, using information related to a physique of the subject, in addition to the virtual grid characteristics received by the receiving unit.

According to a seventh aspect of the invention, in any one of the first to sixth aspects, the derivation unit may derive the imaging conditions of the radiographic image according to virtual grid characteristics which are determined on the basis of the virtual grid characteristics received by the receiving unit and the information related to the physique of the subject.

According to an eighth aspect of the invention, in any one of the first to seventh aspects, the virtual grid characteristics may be a grid ratio.

According to a ninth aspect of the invention, there is provided a radiography method that performs a scattered radiation removal process of removing an influence of scattered radiation included in radiation which has passed through a subject for a radiographic image captured by irradiating the subject with the radiation. The radiography method includes: receiving virtual grid characteristics which are characteristics of a grid virtually used to remove the scattered radiation in the capture of the radiographic image and are used to set an amount of removal of the scattered radiation; and deriving imaging conditions of the radiographic image according to the received virtual grid characteristics.

According to a tenth aspect of the invention, there is provided a radiography program that causes a computer to perform a radiography method which performs a scattered radiation removal process of removing an influence of scattered radiation included in radiation which has passed through a subject for a radiographic image captured by irradiating the subject with the radiation. The radiography program causes the computer to perform: receiving virtual grid characteristics which are characteristics of a grid virtually used to remove the scattered radiation in the capture of the radiographic image and are used to set an amount of removal of the scattered radiation; and deriving imaging conditions of the radiographic image according to the received virtual grid characteristics.

The invention provides a radiography apparatus, a radiography method, and a radiography program that can reduce the burden of an operation related to the setting of imaging conditions on a user.

BRIEF DESCRIPTION OF THE DRAWINGS

FIG. 2 is a diagram illustrating an example of a table indicating a correspondence relationship among virtual grid characteristics, subject information, and imaging conditions.

DESCRIPTION OF EMBODIMENTS

Hereinafter, embodiments of the invention will be described in detail with reference to the drawings. These embodiments do not limit the invention.

First Embodiment

A radiography apparatus according to this embodiment does not have a grid that is provided between a radiation detector and a subject and has a function that performs a virtual grid process of performing image processing for a captured radiographic image to remove the influence of a scattered radiation.

Figure 1:
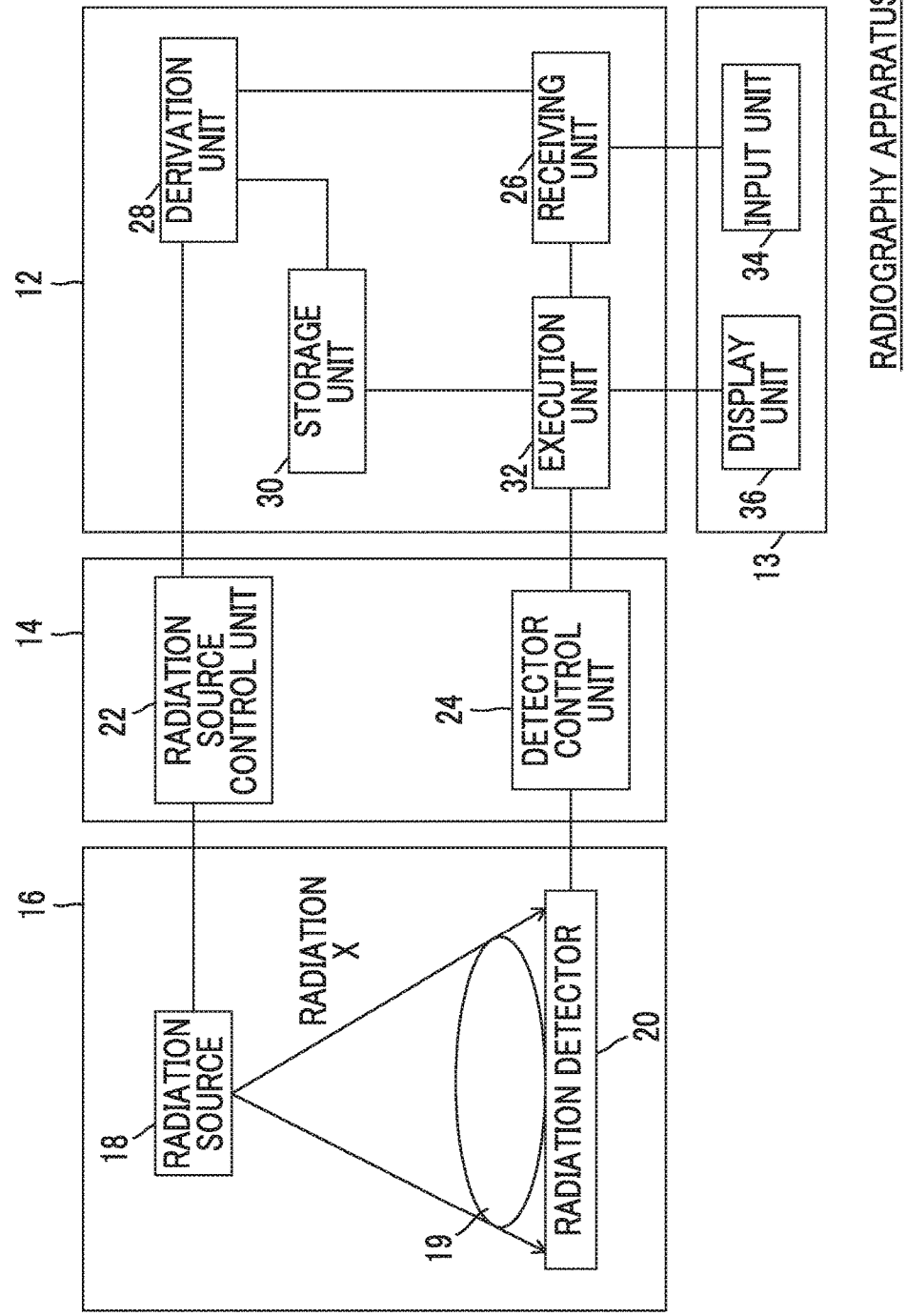
FIG. 1 is a diagram illustrating an example of the structure a radiography apparatus according to a first embodiment.

First, the structure of the radiography apparatus according to this embodiment will be described. FIG. 1 illustrates an example of the structure of the radiography apparatus according to this embodiment. As illustrated in FIG. 1, a radiography apparatus 10 according to this embodiment includes an image processing device 12, a user interface (U/I) unit 13, a control device 14, and an imaging device 16.

The imaging device 16 includes a radiation source 18 and a radiation detector 20. The radiation source 18 has a function of irradiating a subject 19 with radiation X under the control of a radiation source control unit 22. The radiation detector 20 has a function that detects the radiation X which has been emitted from the radiation source 18 and then passed through the subject 19 and outputs a radiographic image of the subject 19. The control device 14 according to this embodiment is a portable electronic cassette and is a so-called flat panel detector (FPD).

The control device 14 includes the radiation source control unit 22 and a detector control unit 24. The radiation source control unit 22 has a function of controlling the driving of the radiation source 18 according to imaging conditions set by the image processing device 12. The detector control unit 24 has a function that controls the radiation detector 20, acquires a radiographic image output from the radiation detector 20, and outputs the radiographic image to the image processing device 12.

The image processing device 12 includes a receiving unit 26, a derivation unit 28, a storage unit 30, and an execution unit 32. The U/I unit 13 includes an input unit 34 and a display unit 36. A console related to the capture of a radiographic image is given as an example of the apparatus including the image processing device 12, the U/I unit 13, and the control device 14 (which will be described below; see FIG. 6).

The input unit 34 is used by a user to input an instruction related to the capture of a radiographic image to the image processing device 12. Examples of the input unit 34 include a keyboard, a mouse, and a touch panel.

The receiving unit 26 has a function of receiving the user's instruction to capture a radiographic image from the input unit 34 of the U/I unit 13. In this embodiment, a person who operates the radiography apparatus 10 or a person who performs radiography, such as a radiological technician or a doctor, is referred to as a "user".

Therefore, the U/I unit 13 has a function of detecting an instruction (operation) which is input by the user through the input unit 34. In this embodiment, the receiving unit 26 has at least a function of receiving an instruction related to virtual grid characteristics which is input by the user through the input unit 34. The virtual grid characteristics are the characteristics of a virtual grid that is assumed to be used in order to perform a virtual grid process which performs image processing for a captured radiographic image to remove the influence of scattered radiation.

In the radiography apparatus 10 according to this embodiment, a grid ratio is used as the virtual grid characteristics. In general, the grid has a structure in which thin lead films having a high absorbance of radiation X and a material (interspace material) which is interposed between the thin lead films and has a low absorbance of radiation X are alternately arranged at a fine grid density of, for example, about 4.0 lines/mm. For example, aluminum, paper, and carbon fiber are used as the interspace material. The grid ratio is defined by the ratio of the heights of the lead films in a case in which the distance between the lead films (the thickness of the interspace material) is "1". When the grid ratio is high, the amount of scattered radiation is effectively reduced. In general, as the tube voltage of the radiation source 18 used becomes higher, a higher grid ratio is used.

The receiving unit 26 according to this embodiment has a function of acquiring information, such as an order related to the capture of a radiographic image, from an external system, such as a radiology information system (RIS), through a communication line or a network, such as a local area network (LAN). Therefore, the U/I unit 13 has a network interface (I/F) function.

The storage unit 30 has a function of storing a table indicating the correspondence relationship among the virtual grid characteristics, the information of the subject 19, and the imaging conditions. In addition, the storage unit 30 according to this embodiment has a function of storing a table in which the virtual grid characteristics received by the receiving unit 26 is associated with information required for the execution unit 32 to perform the virtual grid process. The information for performing the virtual grid process includes scattered radiation transmittance Ts for the virtual grid and primary radiation transmittance Tp which is the transmittance of primary radiation that passes through the subject 19 and is directly emitted to the radiation detector 20. The values of the scattered radiation transmittance Ts and the primary radiation transmittance Tp are in the range of 0 to 1. The virtual grid characteristics are not limited to this embodiment. For example, the virtual grid characteristics may include grid density (lattice density), information indicating whether the grid is a convergence type or a parallel type, a focusing distance in a case in which the grid is a convergence type, and an interspace material.

The storage unit 30 is preferably a non-volatile storage unit and is, for example, a hard disk drive (HDD). FIG. 2 illustrates an example of the table indicating the correspondence relationship among the virtual grid characteristics, the subject information, and the imaging conditions.

As illustrated in FIG. 2, in this embodiment, a tube voltage of the radiation source 18 and the amount of radiation X emitted to the subject 19 (tube current×irradiation time) are used as the imaging conditions. The imaging conditions are not limited thereto and may include, for example, the distance from the radiation source 18 to the radiation detector 20 and the distance from the subject 19 to the radiation detector 20.

The subject information which is an example of information related to the physique of the subject in the disclosed technique is mainly information related to the physique of the subject 19 and includes, for example, age, a body type, and a part to be imaged. The amount of scattered radiation X varies depending on the body type (for example, a normal body type or a fat body type). For example, in the case of the fat body type, that is, when the thickness of the subject 19 (thickness in an irradiation direction) is large, the amount of scattered radiation is large. In addition, the amount of scattered radiation or the distribution thereof varies depending on the part to be imaged (for example, the chest or the abdomen). The physique (body type) of the subject 19 may be estimated from the height and weight of the subject 19. In addition, the subject information may include information related to the position of the subject 19 on a radiographic image and the distribution of the composition of the subject 19.

The derivation unit 28 has a function of deriving the imaging conditions corresponding to the virtual grid characteristics received by the receiving unit 26 on the basis of the table indicating the correspondence relationship which is stored in the storage unit 30. In addition, the derivation unit 28 has a function of setting the derived imaging conditions to the control device 14 (radiation source control unit 22).

The execution unit 32 has a function that acquires the radiographic image captured by the imaging device 16, specifically, the radiographic image output from the radiation detector 20 through the detector control unit 24 and performs the virtual grid process for the acquired radiographic image. The radiographic image that has been subjected to the virtual grid process by the execution unit 32 is displayed on the display unit 36 of the U/I unit 13. The display unit 36 has a function of displaying, for example, information related the capture of a radiographic image and a captured radiographic image. A display, such as a liquid crystal display, is given as an example of the display unit 36.

An example of the virtual grid process which is performed by the execution unit 32 to remove scattered radiation will be described.

The execution unit 32 analyzes the radiographic image which is acquired from the radiation detector 20 through the detector control unit 24 and obtains scattered component information, that is, a scattered radiation content distribution. The execution unit 32 according to this embodiment analyzes the radiographic image on the basis of irradiation field information, the subject information, and the imaging conditions when the radiographic image is captured. The irradiation field information is information indicating an irradiation field distribution related to the position and size of the irradiation field which is included in the radiographic image in a case in which imaging is performed using an irradiation field diaphragm.

As described above, the irradiation field information, the subject information, and the imaging conditions are factors for determining the amount of scattered radiation included in the radiographic image or the distribution of the scattered radiation. For example, as the irradiation field increases and the body thickness of the subject 19 increases, the amount of scattered radiation increases. If there is air between the subject 19 and the radiation detector 20, the amount of scattered radiation decreases. Therefore, the execution unit 32 can accurately acquire the scattered radiation content distribution, using the information related to imaging.

The execution unit 32 calculates a primary radiation image and a scattered radiation image from the body thickness distribution T(x, y) of the subject 19 in the radiographic image, on the basis of the following Expressions (1) and (2). In addition, the execution unit 32 calculates a scattered radiation content distribution S(x, y) from the calculated primary radiation image and scattered radiation image, on the basis of the following Expression (3). The scattered radiation content distribution S(x, y) has a value of 0 to 1.

$$Ip(x,y)=Io(x,y)\times\exp(-\mu\times T(x,y)) \quad (1)$$

$$Is(x,y)=Io(x,y)*S\sigma(T(x,y)) \quad (2)$$

$$S(x,y)=Is(x,y)/(Is(x,y)+Ip(x,y)) \quad (3)$$

In Expressions (1) to (3), (x, y) is the coordinates of a pixel position in a radiographic image, Ip(x, y) is a primary radiation image at the pixel position (x, y), and Is(x, y) is a scattered radiation image at the pixel position (x, y). In addition, Io(x, y) is an incident dose on the surface of the subject 19 at the pixel position (x, y). Furthermore, μ is a linear attenuation coefficient of the subject. Sσ(T(x, y)) is a convolution kernel indicating scattering characteristics corresponding to the body thickness of the subject 19 at the pixel position (x, y). Expression (1) is based on a known exponential attenuation rule and Expression (2) is based on the method described in "J. M. Boon et al., An analytical model of the scattered radiation distribution in diagnostic radiolog, Med. Phys. 15(5), September/October 1988" (Reference Document 1). Even if the incident dose Io(x, y) on the surface of the subject 19 is defined as any value, the incident dose Io(x, y) is cancelled by division when S(x, y) is calculated. Therefore, the incident dose Io(x, y) may be set to an arbitrary value, for example, "1".

The body thickness distribution T(x, y) of the subject 19 may be calculated by converting the pixel value of the radiographic image into a thickness, using the linear attenuation coefficient, on the assumption that a brightness distribution in the radiographic image is substantially identical to the body thickness distribution of the subject 19. Alternatively, the body thickness of the subject 19 may be measured using, for example, a sensor or may be approximated by a model, such as a cube or an elliptic cylinder.

In Expression (2), "*" is an operator indicating a convolution operation. The properties of a kernel change depending on, for example, the distribution of the irradiation field, the distribution of the composition of the subject 19, the imaging conditions, and the characteristics of the radiation detector 20, in addition to the body thickness of the subject 19. According to the method described in Reference Document 1, scattered radiation can be approximated by the convolution of a point spread function (Sσ(T(x, y)) in Expression (2)) with respect to the primary radiation. In addition, Sσ(T(x, y)) can be experimentally calculated on the basis of, for example, the irradiation field information, the subject information, the imaging conditions.

In addition, Sσ(T(x, y)) may be calculated on the basis of the irradiation field information, the subject information, and the imaging conditions during imaging, or may be calculated using a table indicating the correspondence relationship between Sσ(T(x, y)) and various kinds of irradiation field information, various kinds of subject information, and various imaging conditions. In this case, the table indicating the correspondence relationship may be stored in the storage unit 30 in advance and Sσ(T(x, y)) may be calculated on the basis of the irradiation field information, the subject information, and the imaging conditions during imaging, with reference to the table indicating the correspondence relationship which is stored in the storage unit 30. In addition, Sσ(T(x, y)) may be approximated by T(x, y).

The execution unit 32 performs the scattered radiation removal process by reducing a frequency component in a frequency band which is regarded as scattered radiation in the radiographic image, on the basis of the virtual grid characteristics and the scattered component information. The execution unit 32 performs frequency decomposition for the radiographic image to acquire frequency components for each of plural frequency bands and reduces the gain of at least one frequency component. Then, the execution unit 32 synthesizes the processed frequency component and the other frequency components to acquire a radiographic image subjected to the scattered radiation removal process. As a frequency decomposition method, in addition to a method for performing multi-resolution conversion for the radiographic image, other known methods, such as wavelet transform and Fourier transform, can be used.

The execution unit 32 calculates a conversion coefficient R(x, y) for converting a frequency component from the scattered radiation transmittance Ts, the primary radiation transmittance Tp, and the scattered radiation content distribution S(x, y), using the following Expression (4).

$$R(x,y)=S(x,y) \times Ts+(1-S(x,y)) \times Tp \quad (4)$$

Since each of the scattered radiation transmittance Ts, the primary radiation transmittance Tp, and the scattered radiation content distribution S(x, y) has a value of 0 to 1, the conversion coefficient R(x, y) also has a value of 0 to 1. The execution unit 32 calculates the conversion coefficient R(x, y) for each of plural frequency bands.

In the following description, the pixel value of a radiographic image is represented by I(x, y). A frequency component image obtained by frequency decomposition is represented by I(x, y, r). Frequency synthesis is represented by I(x, y)=ΣrI(x, y, r). A conversion coefficient for each frequency band is represented by R(x, y, r). The scattered radiation transmittance and the primary radiation transmittance for each frequency band are represented by Ts(r) and Tp(r), respectively. In addition, "r" indicates a layer of a frequency band. As r becomes greater, the frequency becomes lower. Therefore, I(x, y, r) indicates a frequency component image of a certain frequency band. The scattered radiation content distribution S(x, y) for the radiographic image may be used without any change, or the scattered radiation content distribution S(x, y) may be acquired for each frequency band, similarly to the scattered radiation transmittance Ts and the primary radiation transmittance Tp.

In this embodiment, the execution unit 32 calculates a conversion coefficient R(x, y, r) for each frequency component and multiplies the frequency component image I(x, y, r) by the conversion coefficient R(x, y, r) of a corresponding frequency band to convert the pixel value of the frequency component image I(x, y, r). Then, the execution unit 32 performs frequency synthesis for the frequency component image I(x, y, r) multiplied by the conversion coefficient R(x, y, r) (that is, I(x, y, r)×R(x, y, r)) to acquire a processed radiographic image I'(x, y). Therefore, the process which is performed by the execution unit 32 is represented by the following Expression (5). Since the conversion coefficient R(x, y, r) has a value of 0 to 1, the pixel value of the frequency component at the pixel position (x, y), that is, the gain is reduced by multiplying the frequency component (x, y, r) by the conversion coefficient R(x, y, r) of the corresponding frequency band.

$$I'(x, y) = \sum r\{I(x, y, r) \times R(x, y, r)\} \quad (5)$$
$$= \sum r\{I(x, y, r) \times (S(x, y) \times Ts(r) + (1 - S(x, y)) \times Tp(r))\}$$

In the execution unit 32, a scattered radiation component is removed according to the characteristics (type) of the grid that is assumed to be used, in the processed radiographic image acquired by performing the process illustrated in Expression (5) using the conversion coefficient calculated by the above-mentioned method.

The image processing device 12 according to this embodiment is implemented by, for example, a computer including a central processing unit (CPU), a read only memory (ROM), a random access memory (RAM), and a hard disk drive (HDD). For example, the CPU executes an imaging control process program, which will be described in detail below, to implement the function of the derivation unit 28. In addition, the imaging control process program may be stored in a non-volatile storage unit, such as a ROM, in advance or may be installed in the image processing device 12 through a portable storage unit, such as a universal serial bus (USB) memory, or a line, such as a network.

Next, the imaging control process performed by the image processing device 12 of the radiography apparatus 10 according to this embodiment will be described. The imaging control process corresponds to an example of a radiography method which is a disclosed technique.

Figure 3:
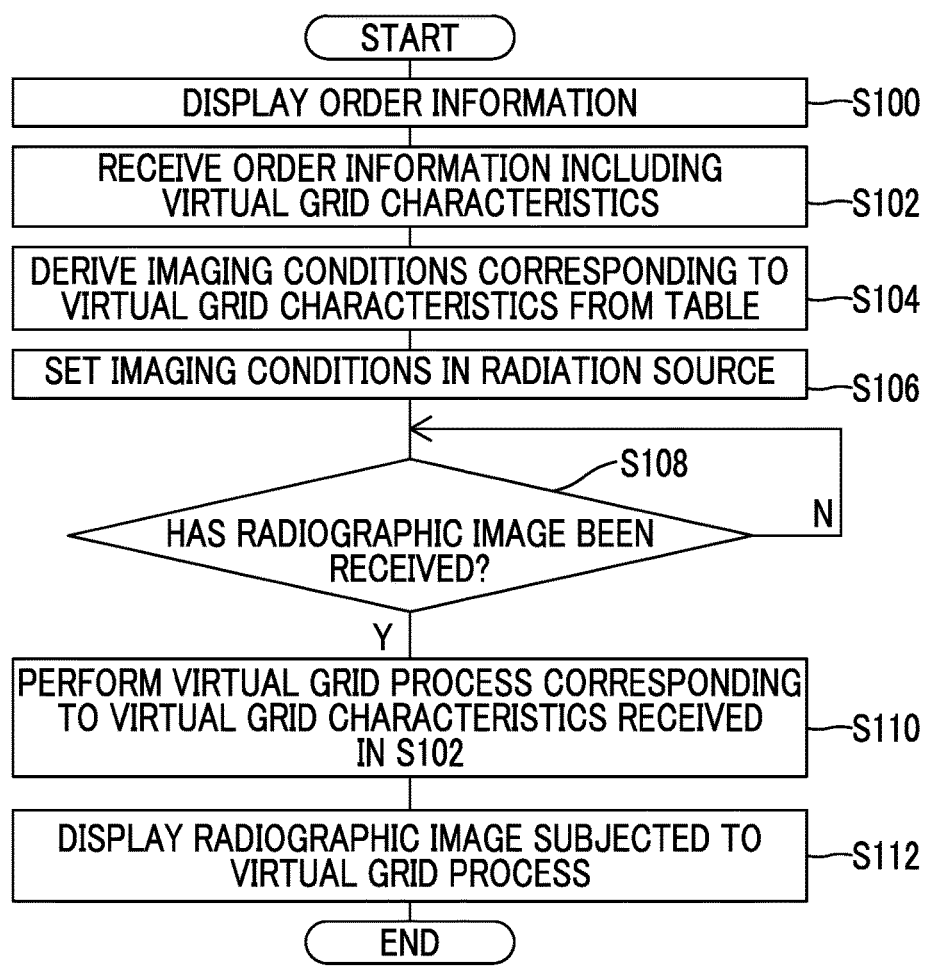
FIG. 3 is a flowchart illustrating an example of an imaging control process according to the first embodiment.

FIG. 3 is a flowchart illustrating an example of the imaging control process according to this embodiment. The imaging control process illustrated in FIG. 3 is performed, for example, in a case in which the receiving unit 26 receives an instruction to capture a radiographic image.

In Step S100, the receiving unit 26 displays order information which is related to the capture of a radiographic image and is received from an external system or the input unit 34 on the display unit 36. Here, examples of the displayed order information include the name or ID of the subject 19 for identifying the subject 19, the part to be imaged, an imaging direction (for example, the front side), and the number of images to be captured. However, the order information is not particularly limited. The order information may be any information for specifying the capture of a radiographic image which will be performed.

The user sets the radiation detector 20 and the radiation source 18 at an imaging position, with the subject 19 interposed therebetween, on the basis of the order information displayed on the display unit 36. In addition, the user inputs the order information including the virtual grid characteristics through the input unit 34. Here, the order information input by the user may be content that is added to the order information displayed in Step S100. However, the invention is not limited to this embodiment. The display of the order information in Step S100 may be omitted and the user may input the order information through the input unit 34. In this embodiment, as described above, for example, the grid ratio is used as the virtual grid characteristics.

Then, in Step S102, the receiving unit 26 receives the order information including the virtual grid characteristics which has been input by the user through the input unit 34 as described above. The received information may be sequentially displayed on the display unit 36 to prompt the user to check the received information.

Then, in Step S104, the derivation unit 28 derives the imaging conditions corresponding to the received virtual grid characteristics, on the basis of the table stored in the storage unit 30. In Example 1 illustrated in FIG. 2, in a case in which a grid ratio of 3:1 is received as the virtual grid characteristics, the derivation unit 28 derives a tube voltage of $\alpha$ kVp, a tube current of $\beta$ mA, and an irradiation time of $\gamma$ msec as the imaging conditions. In a case in which the imaging conditions are derived, the subject information, particularly, the physique (for example, the body type) of the subject 19 may also be considered. As described above, in a case in which the body thickness of the subject 19 is large, it is preferable that the tube voltage of the radiation source 18 is higher than that in a case in which the body thickness is small or in a general case. Therefore, it is preferable to use a table in which imaging conditions that are different from the general (in a case of a general body thickness) imaging conditions (mainly the tube voltage) are associated with the subject information, particularly, the body thickness of the subject 19. For example, in Example 2 illustrated in FIG. 2, unlike Example 1, since the body type is a "fat body type", the tube voltage, which is the imaging conditions, is $\alpha+\theta$ ($\theta>0$) kVp and is higher than that in Example 1.

Then, in Step S106, the derivation unit 28 sets the derived imaging conditions in the radiation source control unit 22 of the control device 14. The radiation source control unit 22 controls the radiation source 18 on the basis of the imaging conditions set by the derivation unit 28 such that a radiographic image is captured.

When the imaging conditions are set, the radiation source control unit 22 controls the radiation source 18 such that the subject 19 is irradiated with the radiation X. The detector control unit 24 controls the radiation detector 20 such that the radiation detector 20 detects the radiation X transmitted through the subject 19 and outputs a radiographic image indicating an image of the subject 19 to the detector control unit 24.

Then, in Step S108, the execution unit 32 determines whether a radiographic image has been received from the radiation detector 20 through the detector control unit 24. In a case in which a radiographic image has not been received, for example, in a case in which a radiographic image is being captured, the execution unit 32 is in a standby state. On the other hand, when a radiographic image has been received, the process proceeds to Step S110.

In Step S110, the execution unit 32 performs the virtual grid process corresponding to the virtual grid characteristics received by the receiving unit 26 in Step S102 for the received radiographic image to remove the influence of scattered radiation from the radiographic image. Specifically, the execution unit 32 acquires the scattered radiation transmittance Ts and the primary radiation transmittance Tp corresponding to the received virtual grid characteristics (grid ratio) from the table indicating the correspondence relationship which is stored in the storage unit 30. In addition, the execution unit 32 acquires the imaging conditions derived by the derivation unit 28 from the derivation unit 28. Then, the execution unit 32 performs the virtual grid process on the basis of the scattered radiation transmittance Ts, the primary radiation transmittance Tp, and the imaging conditions, using Expressions (1) to (5).

Then, in Step S112, the execution unit 32 displays a radiographic image, from which the influence of scattered radiation has been removed by the virtual grid process, on the display unit 36 and ends the process.

After Step S104 or before a radiographic image is captured after Step S106, the user may finely adjust the imaging conditions. For example, in a case in which the physique of the subject 19 is normal and the thickness of the part to be imaged is slightly larger than that of a normal body type, the user may determine whether to adjust the imaging conditions such as the tube voltage. When the imaging conditions are adjusted, the derivation unit 28 may acquire an adjustment instruction, which is input by the user through the input unit 34, through the receiving unit 26 and instruct the radiation source control unit 22 to adjust the set imaging conditions on the basis of the acquired adjustment instruction. In addition, the imaging device 16 may include, for example, a sensor (not illustrated) that measures the body thickness of the subject 19 and the derivation unit 28 or the radiation source control unit 22 may finely adjust the imaging conditions on the basis of the body thickness measured by the sensor. In a case in which the imaging conditions are adjusted, the execution unit 32 performs the virtual grid process on the basis of the adjusted imaging conditions in Step S110.

Second Embodiment

Next, a second embodiment will be described. The same components as those in the radiography apparatus 10 according to the first embodiment are denoted by the same reference numerals and the detailed description thereof will not be repeated.

Since the structure of a radiography apparatus 10 is the same as that in the first embodiment (see FIG. 1), the description thereof will not be repeated. An imaging control process of the radiography apparatus 10 according to this embodiment includes processes different from those in the imaging control process according to the first embodiment (see FIG. 3). Therefore, different processes will be described.

Figure 4:
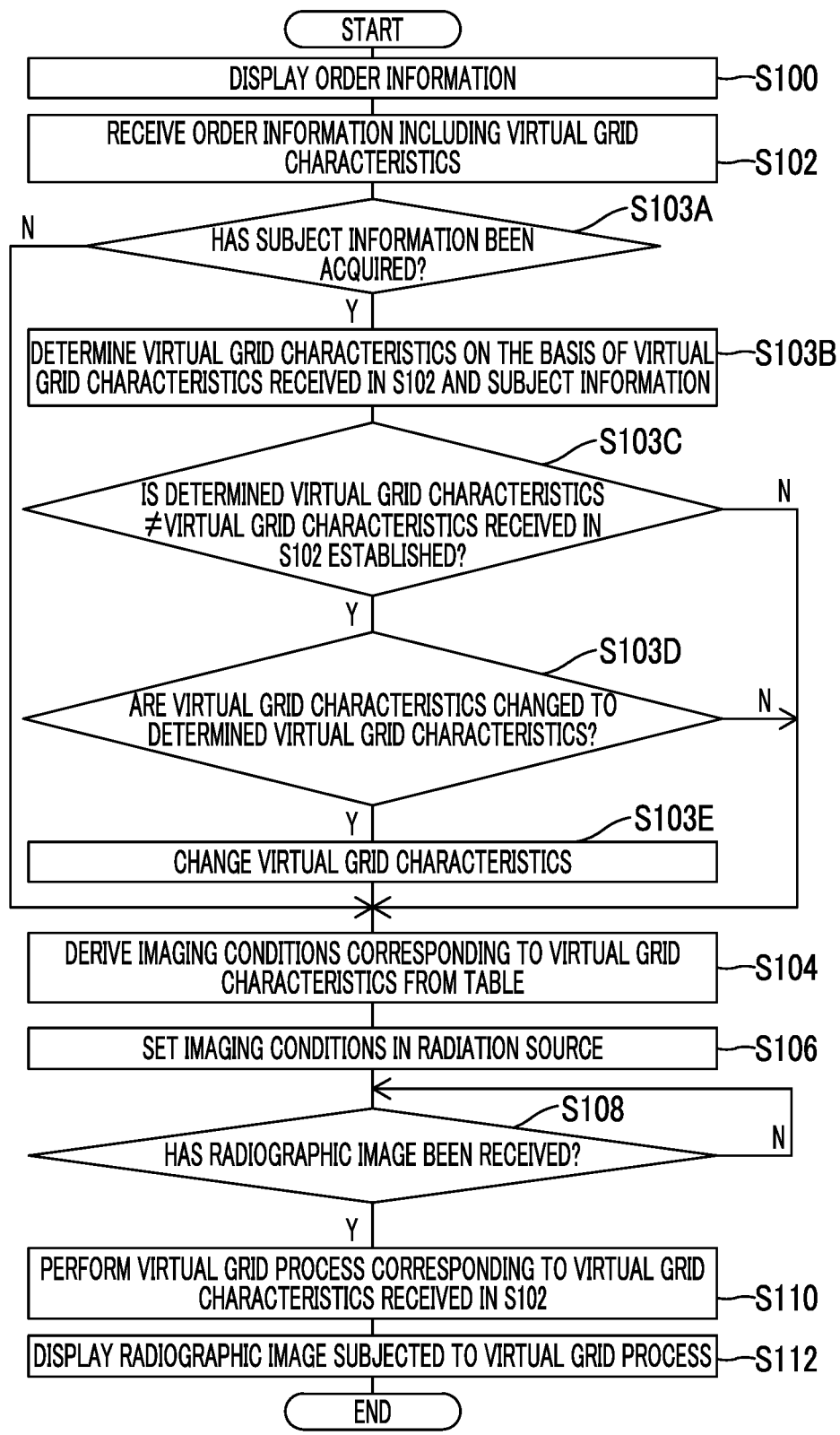
FIG. 4 is a flowchart illustrating an example of an imaging control process according to a second embodiment.

FIG. 4 is a flowchart illustrating an example of the imaging control process according to this embodiment. The imaging control process according to this embodiment differs from the imaging control process according to the first embodiment in that, in a case in which subject information is acquired in the imaging control process according to the first embodiment (see FIG. 3), the virtual grid characteristics are determined on the basis of the subject information and imaging conditions are set on the basis of the determined virtual grid characteristics. Therefore, as illustrated in FIG. 4, the imaging control process according to this embodiment includes Steps S103A to S103E between Step S102 and Step S104. The other processes from Step S100 to Step S112 are the same as those from Step S100 to Step S112 in the first embodiment.

That is, the receiving unit 26 displays order information related to the capture of a radiographic image on the display unit 36. The user sets the radiation detector 20 and the radiation source 18 at an imaging position, with the subject 19 interposed therebetween, on the basis of the display of the order information. In addition, the user inputs the order information including the virtual grid characteristics (grid ratio) through the input unit 34. The receiving unit 26 receives the order information including the virtual grid characteristics.

After the above-mentioned processes, the imaging control process according to this embodiment proceeds to Step S103A. In Step S103A, the derivation unit 28 determines whether subject information has been acquired. For example, in a case in which the user determines that the subject 19 is a fat body type, the user inputs subject information indicating a "fat" body type through the input unit 34. For example, in a case in which the receiving unit 26 receives the subject information from the input unit 34 or in a case in which the subject information is included in the order information, the subject information is acquired and the process proceeds to Step S103B. On the other hand, when the subject information is not acquired, the process proceeds to Step S104.

In Step S103B, the derivation unit 28 determines virtual grid characteristics from the table stored in the storage unit 30 on the basis of the virtual grid characteristics received in Step S102 and the acquired subject information. For example, in a case in which a virtual grid characteristic of 3:1 is received and a "normal body type" is acquired as the subject information, a virtual grid characteristic of 3:1 is determined as in Example 1. For example, in a case in which a virtual grid characteristic of 3:1 is received and a "fat body type" is acquired as the subject information, a virtual grid characteristic of 4:1 is determined as in Example 2.

Then, in Step S103C, the derivation unit 28 determines whether the virtual grid characteristics determined in Step S103B are not identical (≠) to the virtual grid characteristics received in Step S102. In a case in which the virtual grid characteristics are not identical to each other, the process proceeds to Step S104. In a case in which the virtual grid characteristics are identical to each other, the process proceeds to Step S103D.

Then, in Step S103D, the derivation unit 28 determines whether to change the virtual grid characteristics to the virtual grid characteristics determined in Step S103B. A method for determining whether to change the virtual grid characteristics to the determined virtual grid characteristics is not particularly limited. For example, information inquiring of the user whether to change the virtual grid characteristics may be displayed on the display unit 36 and it may be determined whether to change the virtual grid characteristics on the basis of the inquiry result which is received from the user by the receiving unit 26. For example, in a case in which whether to change the virtual grid characteristics to the determined virtual grid characteristics is set in the derivation unit 28 in advance, it may be determined whether to change the virtual grid characteristics on the basis of the setting.

In a case in which the virtual grid characteristics are not changed to the determined virtual grid characteristics, the process proceeds to Step S104. On the other hand, in a case in which the virtual grid characteristics are changed to the determined virtual grid characteristics, the process proceeds to Step S103E. In Step S103E, the derivation unit 28 changes the virtual grid characteristics. Specifically, the derivation unit 28 changes the virtual grid characteristics received in Step S102 to the virtual grid characteristics determined in Step S103B.

Then, in Step S104, the derivation unit 28 derives imaging conditions corresponding to the virtual grid characteristics on the basis of the table stored in the storage unit 30. Here, in a case in which the virtual grid characteristics are changed in Step S103E, the derivation unit 28 derives imaging conditions corresponding to the changed virtual grid characteristics, that is, the virtual grid characteristics determined in Step S103B. In a case in which the virtual grid characteristics are not changed, the derivation unit 28 derives imaging conditions corresponding to the virtual grid characteristics received in Step S102. That is, the derivation unit 28 derives imaging conditions corresponding to the virtual grid characteristics received in the Step S102 in a case in which the subject information is not acquired, the determined virtual grid characteristics are identical to the virtual grid characteristics received in Step S102, and it is determined that the virtual grid characteristics are not changed to the virtual grid characteristics determined in Step S103D.

The subsequent process in Steps S106 to S112 is the same as the process in Steps S106 to Step S112 (see FIG. 3) according to the first embodiment.

That is, the derivation unit 28 sets the derived imaging conditions in the radiation source control unit 22 of the control device 14. The radiation source control unit 22 controls the radiation source 18 on the basis of the imaging conditions set by the derivation unit 28 such that a radiographic image is captured. When receiving the radiographic image captured by the radiation detector 20, the execution unit 32 performs a virtual grid process on the basis of the scattered radiation transmittance Ts, the primary radiation transmittance Tp, and the imaging conditions corresponding to the received virtual grid characteristics, using Expressions (1) to (5). In addition, the execution unit 32 displays the radiographic image from which the influence of scattered radiation has been removed by the virtual grid process on the display unit 36.

Third Embodiment

Next, a third embodiment will be described. The same components as those in the radiography apparatus 10 according to each of the above-described embodiments are denoted by the same reference numerals and the detailed description thereof will not be repeated.

The structure of a radiography apparatus 10 is the same as that in the first embodiment (see FIG. 1) and thus the description thereof will not be repeated. An imaging control process of the radiography apparatus 10 according to this embodiment includes processes different from those in the imaging control process according to each of the above-described embodiments (see FIGS. 3 and 4). Therefore, different processes will be described.

Figure 5:
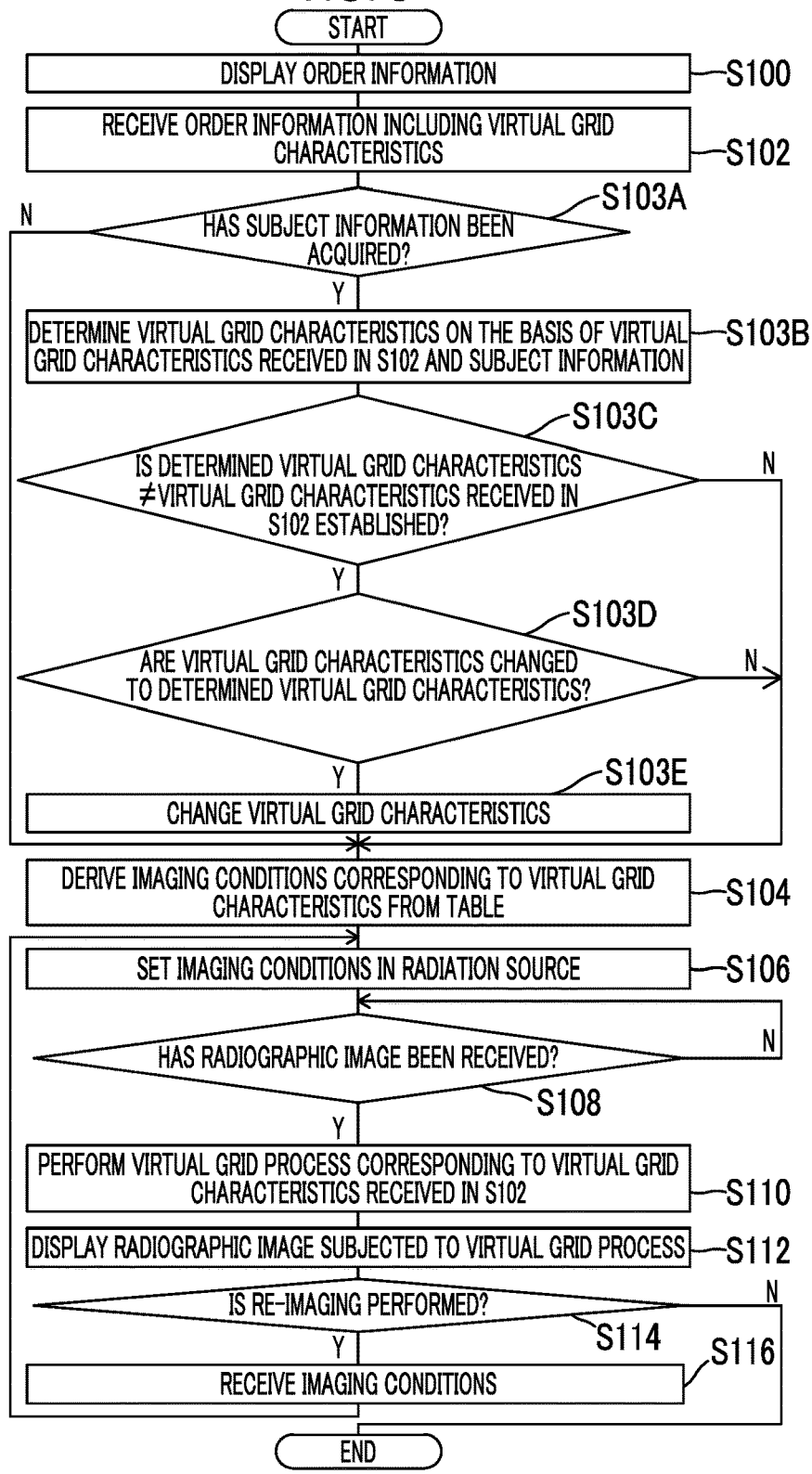
FIG. 5 is a flowchart illustrating an example of an imaging control process according to a third embodiment.

FIG. 5 is a flowchart illustrating an example of the imaging control process according to this embodiment. The imaging control process according to this embodiment differs from the imaging control process according to the second embodiment in that it includes a process in a case in which re-imaging is performed after a radiographic image is displayed in the imaging control process according to the second embodiment. Therefore, as illustrated in FIG. 5, in the imaging control process according to this embodiment, a process from Step S100 to Step S112 is the same as the process from Step S100 to Step S112 (see FIG. 4) according to the second embodiment.

That is, the receiving unit 26 displays order information related to the capture of a radiographic image on the display unit 36. The user sets the radiation detector 20 and the radiation source 18 at an imaging position, with the subject 19 interposed therebetween, on the basis of the display of the order information. In addition, the user inputs order information including the virtual grid characteristics (grid ratio) through the input unit 34. The receiving unit 26 receives the order information including the virtual grid characteristics.

When subject information is acquired, the derivation unit 28 determines virtual grid characteristics from the table stored in the storage unit 30 on the basis of the virtual grid characteristics received in Step S102 and the acquired subject information. In a case in which the determined virtual grid characteristics are not identical to the received virtual grid characteristics and the virtual grid characteristics are changed to the determined virtual grid characteristics, the derivation unit 28 changes the virtual grid characteristics. Then, the derivation unit 28 derives imaging conditions corresponding to the virtual grid characteristics from the table stored in the storage unit 30. In a case in which the virtual grid characteristics are changed, the derivation unit 28 derives imaging conditions corresponding to the changed virtual grid characteristics (determined virtual grid characteristics).

The derivation unit 28 sets the derived imaging conditions in the radiation source control unit 22 of the control device 14. The radiation source control unit 22 controls the radiation source 18 on the basis of the imaging conditions set by the derivation unit 28 such that a radiographic image is captured. When the radiographic image captured by the radiation detector 20 is received, the execution unit 32 performs the virtual grid process on the basis of the scattered radiation transmittance Ts, the primary radiation transmittance Tp, and the imaging conditions corresponding to the received virtual grid characteristics, using Expressions (1) to (5). In addition, the execution unit 32 displays the radiographic image from which the influence of scattered radiation has been removed by the virtual grid process on the display unit 36.

The imaging control process according to this embodiment proceeds to Step S114 after the above-mentioned processes. In Step S114, it is determined whether to perform re-imaging. In a case in which the user checks the radiographic image displayed on the display unit 36 in Step S112 and performs re-imaging for the reason that the radiographic image is not preferable, the user inputs a re-imaging instruction through the input unit 34. In a case in which the receiving unit 26 does not receive the re-imaging instruction from the input unit 34 (in a case in which the user does not input the re-imaging instruction), the process ends. On the other hand, in a case in which the receiving unit 26 receives the re-imaging instruction from the input unit 34, the process proceeds to Step S116.

In Step S116, the receiving unit 26 receives the changed imaging conditions. As described above, for example, in a case in which the radiographic image is undesirable, the imaging conditions are not appropriate during imaging. Examples of the case include a case in which the amount of radiation that is more or less than that set by the radiation source control unit 22 is emitted to the subject 19 due to the deterioration of a bulb of the radiation source 18 and a case in which the body thickness of the subject 19 is large. Therefore, in some cases, it is preferable to change the imaging conditions during re-imaging. The user inputs re-imaging conditions through the input unit 34. In this case, in order to facilitate a change in the imaging conditions, the current imaging conditions may be displayed on the display unit 36 so as to be presented to the user.

Then, in Step S116, the receiving unit 26 receives the imaging conditions. Then, the process returns to Step S106 and is repeatedly performed.

That is, in Step S106, the derivation unit 28 sets the received re-imaging conditions in the radiation source control unit 22. Then, in Step S108, the execution unit 32 determines whether a radiographic image has been received. When the execution unit 32 has received, the execution unit 32 performs the virtual grid process corresponding to the virtual grid characteristics received in Step S102 for the received radiographic image in Step S110. Then, in Step S112, the execution unit 32 displays a re-captured radiographic image from which the influence of scattered radiation has been removed by the virtual grid process on the display unit 36. As such, in the case of re-imaging, the derivation unit 28 according to this embodiment performs the virtual grid process, using the virtual grid characteristics (grid ratio) used in the initial imaging process. For example, in some cases, the imaging conditions during re-imaging correspond to a grid ratio of 6:1 in the table indicating the correspondence relationship illustrated in FIG. 2. In this case, the derivation unit 28 of the image processing device 12 according to this embodiment performs the virtual grid process, using the virtual grid characteristics (grid ratio) used in the initial imaging process.

The radiography apparatus 10 (image processing device 12) according to this embodiment does not prevent the virtual grid process from being performed using virtual grid characteristics (grid ratio) different from the virtual grid characteristics (grid ratio) acquired in Step S102. For example, the virtual grid characteristics (grid ratio) may be changed in response to an instruction from the user who has checked the radiographic image displayed on the display unit 36 in Step S112 and the execution unit 32 may perform the virtual grid process and display the radiographic image from which the influence of scattered radiation has removed on the display unit 36.

In this embodiment, for example, the determined virtual grid characteristics are displayed on the display unit 36 and it is determined whether to change the virtual grid characteristics. However, the invention is not limited thereto. For example, the subject information (body type) may be displayed on display unit 36 to inquire of the user whether to change the virtual grid characteristics and the virtual grid characteristics may be determined or changed on the basis of the inquiry result from the user.

In this embodiment, re-imaging is performed in the imaging control process according to the second embodiment. However, the invention is not limited thereto. For example, the invention may be applied to a case in which re-imaging is performed in the imaging control process according to the first embodiment.

As described above, in the radiography apparatus 10 according to each of the above-described embodiments, the image processing device 12 includes the receiving unit 26, the derivation unit 28, the storage unit 30, and the execution unit 32. The receiving unit 26 receives the virtual grid characteristics from the input unit 34. The derivation unit 28 derives the imaging conditions corresponding to the received virtual grid characteristics (grid ratio) on the basis of the table stored in the storage unit 30. The derivation unit 28 sets the derived imaging conditions in the radiation source control unit 22. The radiation source control unit 22 controls the radiation source 18 on the basis of the set imaging conditions such that a radiographic image is captured. The execution unit 32 of the image processing device 12 acquires the radiographic image captured by the radiation detector 20 through the detector control unit 24. The execution unit 32 performs the virtual grid process for the acquired radiographic image on the basis of the virtual grid characteristics received by the receiving unit 26 and the imaging conditions derived by the derivation unit 28 to generate a radiographic image from which the influence of scattered radiation has been removed and displays the radiographic image on the display unit 36.

As such, in the radiography apparatus 10 according to each of the above-described embodiments, the derivation unit 28 derives the imaging conditions corresponding to the virtual grid characteristics received by the receiving unit 26 and sets the imaging conditions in the radiation source control unit 22. Therefore, it is possible to reduce the burden of an operation related to the setting of the imaging conditions on the user.

Figure 6:
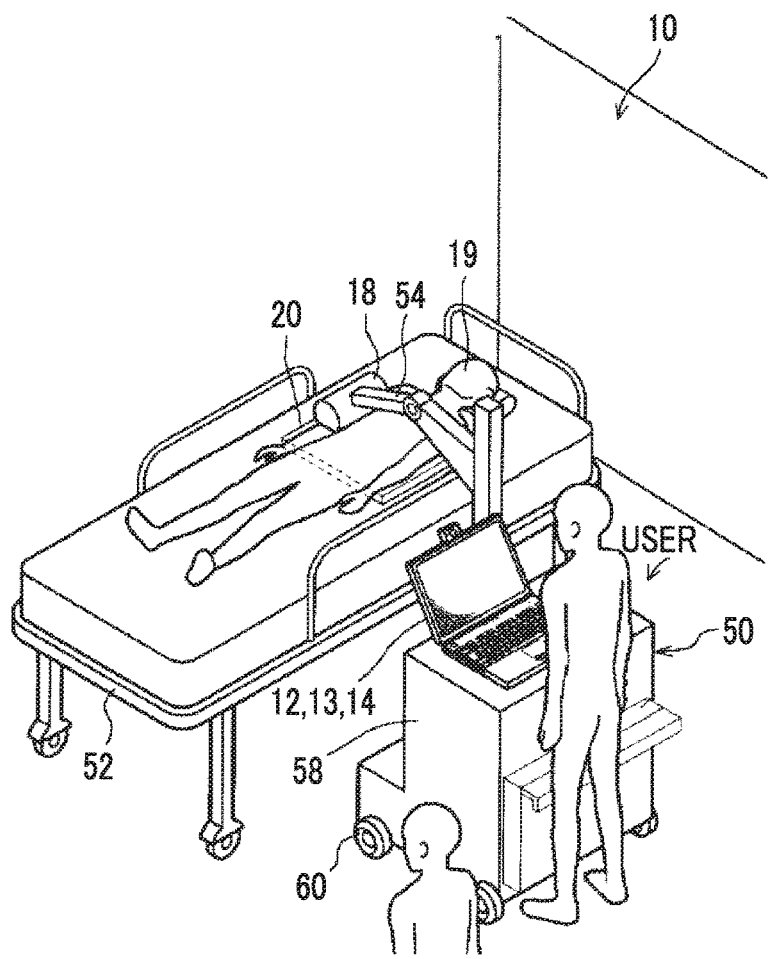
FIG. 6 is a diagram illustrating an example of a state in which the radiography apparatus according to each embodiment is applied to a medical cart and is arranged in a hospital room of a subject.

In the radiography apparatus 10 according to each of the above-described embodiments, the execution unit 32 acquires the radiographic image which has been captured, without actually providing a grid between the radiation detector 20 and the subject 19, and performs the virtual grid process as image processing for the acquired radiographic image to remove the influence of scattered radiation from the radiographic image. As described above, in the grid which is actually provided between the radiation detector 20 and the subject 19, interspace materials, such as lead and aluminum, are alternately arranged at a fine grid density. Therefore, the grid is weighty. For this reason, for example, as illustrated in FIG. 6 which will be described in detail below, the grid needs to be provided between the lying subject 19 and the radiation detector 20, which causes an increase in the burden of an arrangement operation and an increase in strain on the subject 19 during imaging. Further, in the case of a convergence-type grid, density unevenness is likely to occur in the radiographic image due to the oblique incidence of radiation. In addition, a subject image and a fine stripe pattern (moire) corresponding to the pitch of the grid are recorded on the radiographic image, which makes it difficult to see the radiographic image. For example, the technique disclosed in JP-A No. 2013-172881 has been known as image processing according to the related art which removes a stripe pattern. In the related art, in some cases, the processing time increases. In contrast, the radiography apparatus 10 according to each of the above-described embodiments performs the virtual grid process based on the virtual grid characteristics to remove the influence of scattered radiation from the radiographic image, without actually using a grid, similarly to the case in which a grid is provided. Therefore, it is possible to further reduce the burden of the subject 19 or the user. In addition, it is possible to prevent the problem that the radiographic image is difficult to see due to, for example, moire.

In the radiography apparatus 10, the execution unit 32 performs the virtual grid process on the basis of the virtual grid characteristics received by the receiving unit 26. Therefore, it is possible to instruct the virtual grid characteristics that are assumed to be used to control the amount of removal of scattered radiation.

The radiography apparatus 10 according to the first embodiment sets the imaging conditions on the basis of the virtual grid characteristics received in Step S102. Therefore, for example, the virtual grid process corresponding to the virtual grid characteristics desired by the user is performed. As a result, it is possible to reduce the burden of the user which desires a virtual grid process corresponding to desired virtual grid characteristics.

The radiography apparatus 10 according to the second and third embodiments determines the virtual grid characteristics on the basis of the virtual grid characteristics received in Step S102 and the subject information, derives the imaging conditions corresponding to the determined virtual grid characteristics, and sets the imaging conditions. Therefore, it is possible to further reduce the burden of the user and to appropriately remove the influence of scattered radiation from a radiographic image.

In each of the above-described embodiments, the radiation detector 20 is an FPD. However, the invention is not limited thereto. The radiation detector may be other types. In addition, the structure of the radiography apparatus 10 is not particularly limited. It is preferable that the radiography apparatus 10 is applied to a medical cart. FIG. 6 illustrates an example of a state in which the radiography apparatus 10 is applied to a medical cart and is provided in a hospital room of the subject 19.

As illustrated in FIG. 6, the radiography apparatus 10 according to each of the above-described embodiments include the radiation detector 20 and a medical cart 50. The medical cart 50 includes the radiation source 18, the image processing device 12 that functions as a console, the U/I unit 13, and the control device 14. The radiation detector 20 is provided between a bed 52 and a patient as the subject 19 who lies on his or her back on the bed 52. The medical cart 50 according to each of the above-described embodiments include an arm 54 and the radiation source 18 is provided at one end of the arm 54. The radiation source 18 is provided above the subject 19 who lies on his or her back on the bed 52. In addition, the medical cart 50 includes wheels 60 that are provided at the bottom of a main body 58 and is movable in the hospital. When an instruction to capture a radiographic image is input through the U/I unit 13, the medical cart 50 captures a radiographic image on the basis of the imaging conditions, using the radiation detector 20, under the control of the image processing device 12 and the control device 14.

In each of the above-described embodiments, the storage unit 30 stores two tables, that is, the table indicating the correspondence relationship among the virtual grid characteristics, the information of the subject 19, and the imaging conditions and the table in which the virtual grid characteristics are associated with information used by the execution unit 32 to perform the virtual grid process. However, the tables may be stored in different storage units.

In each of the above-described embodiments, radiation is not particularly limited. For example, X-rays or γ-rays may be applied.

In addition, for example, the structure and operation of the radiography apparatus 10 according to each of the above-described embodiments are illustrative and can be changed according to the situation, without departing from the scope and spirit of the invention.

The entire disclosure of Japanese Patent Application No. 2014-070544 is incorporated herein by reference.

All of the documents, the patent applications, and the technical standards mentioned in the specification are incorporated herein by reference to the same extent as that in a case in which the incorporation of the documents, the patent applications, and the technical standards by reference is specifically and individually mentioned.

What is claimed is:

1. A radiography apparatus that performs a scattered radiation removal process of removing an influence of scattered radiation included in radiation which has passed through a subject for a radiographic image captured by irradiating the subject with the radiation, comprising:
    a receiving unit that receives virtual grid characteristics which are characteristics of a grid virtually used to remove the scattered radiation in the capture of the radiographic image and are used to set an amount of removal of the scattered radiation;
    a derivation unit that derives imaging conditions of the radiographic image according to the virtual grid characteristics received by the receiving unit; and
    an imaging unit that captures the radiographic image under the imaging conditions derived by the derivation unit.

2. The radiography apparatus according to claim 1, further comprising:
    an execution unit that performs the scattered radiation removal process for the radiographic image captured by the imaging unit with an amount of removal corresponding to the virtual grid characteristics.

3. The radiography apparatus according to claim 2, wherein, during a re-imaging process, the execution unit performs the scattered radiation removal process on the basis of the virtual grid characteristics received in a previous imaging process.

4. The radiography apparatus according to claim 1, further comprising:
    a storage unit that stores the virtual grid characteristics and the imaging conditions corresponding to the virtual grid characteristics so as to be associated with each other,
    wherein the derivation unit reads the imaging conditions corresponding to the virtual grid characteristics received by the receiving unit from the storage unit and derives the imaging conditions.

5. The radiography apparatus according to claim 1, wherein the derivation unit derives the imaging conditions, using information related to a physique of the subject, in addition to the virtual grid characteristics received by the receiving unit.

6. The radiography apparatus according to claim 1, wherein the derivation unit derives the imaging conditions of the radiographic image according to virtual grid characteristics which are determined on the basis of the virtual grid characteristics received by the receiving unit and information related to a physique of the subject.

7. The radiography apparatus according to claim 1, wherein the virtual grid characteristics are a grid ratio.

8. A radiography method that performs a scattered radiation removal process of removing an influence of scattered radiation included in radiation which has passed through a subject for a radiographic image captured by irradiating the subject with the radiation, comprising:
    receiving virtual grid characteristics which are characteristics of a grid virtually used to remove the scattered radiation in the capture of the radiographic image and are used to set an amount of removal of the scattered radiation;
    deriving imaging conditions of the radiographic image according to the received virtual grid characteristics; and
    capturing, via an imaging unit, the radiographic image under the derived imaging conditions.

9. A non-transitory computer readable medium storing a radiography program that causes a computer to perform a radiography method which performs a scattered radiation removal process of removing an influence of scattered radiation included in radiation which has passed through a subject for a radiographic image captured by irradiating the subject with the radiation and to perform:
    receiving virtual grid characteristics which are characteristics of a grid virtually used to remove the scattered radiation in the capture of the radiographic image and are used to set an amount of removal of the scattered radiation;
    deriving imaging conditions of the radiographic image according to the received virtual grid characteristics; and
    capturing, via an imaging unit, the radiographic image under the derived imaging conditions.

* * * * *